(12) United States Patent
Tang et al.

(10) Patent No.: US 12,000,828 B2
(45) Date of Patent: Jun. 4, 2024

(54) IMMUNODETECTION CHIP, IMMUNODETECTION DEVICE AND USING METHOD

(71) Applicant: BOE Technology Group Co., Ltd., Beijing (CN)

(72) Inventors: Hao Tang, Beijing (CN); Quanguo Zhou, Beijing (CN); Jiuyang Cheng, Beijing (CN); Lijia Zhou, Beijing (CN); Zhidong Wang, Beijing (CN); Yancheng Lu, Beijing (CN); Ronghua Lan, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 653 days.

(21) Appl. No.: 16/758,163

(22) PCT Filed: Mar. 25, 2019

(86) PCT No.: PCT/CN2019/079599
§ 371 (c)(1),
(2) Date: Apr. 22, 2020

(87) PCT Pub. No.: WO2020/191602
PCT Pub. Date: Oct. 1, 2020

(65) Prior Publication Data
US 2021/0215688 A1    Jul. 15, 2021

(51) Int. Cl.
*G01N 33/543* (2006.01)
*G01N 27/74* (2006.01)

(52) U.S. Cl.
CPC ..... *G01N 33/54326* (2013.01); *G01N 27/745* (2013.01); *G01N 33/54386* (2013.01)

(58) Field of Classification Search
CPC .......... G01N 33/54386; G01N 27/745; G01N 33/54326; G01N 2470/04;
(Continued)

(56) References Cited

U.S. PATENT DOCUMENTS

| 6,180,418 B1 | 1/2001 | Lee |
| 7,736,889 B2 | 6/2010 | Rife et al. |

(Continued)

FOREIGN PATENT DOCUMENTS

| CN | 101981448 A | 2/2011 |
| CN | 102937649 A | 2/2013 |

(Continued)

OTHER PUBLICATIONS

"Rapid integrated biosensor for multiplexed immunoassays based on actuated magnetic nanoparticles Lab on a Chip", Bruls et al. The Royal Society of Chemisry 2009, vol. 9, 3504-3510.
(Continued)

*Primary Examiner* — Christopher L Chin
(74) *Attorney, Agent, or Firm* — ArentFox Schiff LLP; Michael Fainberg

(57) ABSTRACT

An embodiment of the disclosure provides an immunodetection chip, an immunodetection device and a using method. The immunodetection chip includes a substrate and a cover plate. The substrate is disposed opposite to the cover plate to form a detection chamber. One side, facing the cover plate, of the substrate is fixedly provided with substrate antibodies. An inside wall of the detection chamber is provided with a detection member. The detection member is configured to output a corresponding electrical signal while adsorbing biological magnetic beads. The substrate antibodies match with target antigens.

6 Claims, 8 Drawing Sheets

(58) Field of Classification Search
CPC ........... G01N 33/54306; G01N 27/327; G01N 27/3275; G01N 29/2437; G01N 29/2462; G01N 29/022; G01N 29/032; G01N 29/036; G01N 2446/20; G01N 2446/80; H10N 30/00; H10N 30/1071; H10N 30/30; H10N 30/302; B01L 2300/0627; B01L 2300/0636; B01L 2300/0819
USPC ........ 310/313 R, 340; 422/82.01; 435/287.2, 435/287.9; 436/526, 806
See application file for complete search history.

(56) References Cited

U.S. PATENT DOCUMENTS

| | | | |
|---|---|---|---|
| 2006/0263894 A1* | 11/2006 | Carter | G01N 33/54366 436/149 |
| 2009/0170212 A1* | 7/2009 | Van Der Wijk | G01R 33/093 422/82.01 |
| 2011/0104708 A1 | 5/2011 | Carter et al. | |
| 2013/0309779 A1 | 11/2013 | Kasai et al. | |
| 2015/0177239 A1* | 6/2015 | Evers | G01N 33/54393 435/7.1 |
| 2016/0123965 A1 | 5/2016 | Evers et al. | |
| 2017/0045505 A1* | 2/2017 | Munge | G01N 33/581 |
| 2019/0018011 A1 | 1/2019 | Iwata | |

FOREIGN PATENT DOCUMENTS

| | | |
|---|---|---|
| CN | 103344754 A | 10/2013 |
| CN | 103364543 A | 10/2013 |
| CN | 103424554 A | 12/2013 |
| CN | 103946686 A | 7/2014 |
| CN | 105579849 A | 5/2016 |
| WO | 2011045570 A2 | 4/2011 |
| WO | 2013072842 A1 | 5/2013 |
| WO | 2018077804 A1 | 5/2018 |

OTHER PUBLICATIONS

Chinese Office Action 201980000369.3 dated Dec. 26, 2023.

* cited by examiner

IMMUNODETECTION CHIP, IMMUNODETECTION DEVICE AND USING METHOD

The present application is a US National Stage of International Application No. PCT/CN2019/079599, filed on Mar. 25, 2019, and entitled "Immunodetection Chip, Immunodetection Device and Using Method", the content of which is incorporated by reference herein in its entirety.

FIELD

The disclosure relates to the technical field of immunodetection analysis and in particular relates to an immunodetection chip, an immunodetection device and a using method.

BACKGROUND

Currently, immunodetection methods mainly include immunofluorescence technique, radio immunoassay technique, chemiluminescence immunoassay, and immune colloidal gold technique, etc. However, immunodetection of the prior art has problems of high detection cost, many limitations and complicated detection steps.

SUMMARY

An immunodetection chip provided by an embodiment of the disclosure includes:
a substrate, and
a cover plate;
where the substrate is disposed opposite to the cover plate to form a detection chamber; one side, facing the cover plate, of the substrate is fixedly provided with substrate antibodies, and an inside wall of the detection chamber is provided with a detection member;
the detection member is configured to output a corresponding electrical signal while adsorbing biological magnetic beads; and
the substrate antibodies match with target antigens.

Optionally, the detection member is located on one side, facing the substrate, of the cover plate.

Optionally, the detection member is located between the substrate and the substrate antibodies.

Optionally, a biological modification layer is disposed between the substrate antibodies and the detection member.

Optionally, the biological modification layer is made of nanogold or a high molecular polymer material.

The embodiment of the disclosure further provides an immunodetection device, including the immunodetection chip provided by the embodiment of the disclosure.

Optionally, the immunodetection device further includes biological magnetic beads, where the biological magnetic beads each includes a magnetic bead and magnetic bead antibodies enveloping the magnetic bead, and the biological magnetic beads are added to the detection chamber of the immunodetection chip while being used to detect the antigens to be detected.

Optionally, the immunodetection device further includes a magnetic field generation member that applies a magnetic field to the immunodetection chip while being used to detect the antigens to be detected.

Optionally, the magnetic field generation member is located on one side, facing away from the substrate, of the cover plate.

Optionally, the magnetic field generation member is located on one side, facing away from the cover plate, of the substrate.

The embodiment of the disclosure further provides a using method of the immunodetection chip provided by the embodiment of the disclosure, including the steps of:
adding biological magnetic beads and liquid including antigens to be detected to a detection chamber, where the biological magnetic beads each includes a magnetic bead and magnetic bead antibodies enveloping the magnetic bead and matching with the target antigens, a substrate of the detection chamber is fixedly provided with substrate antibodies, and the substrate antibodies and the magnetic bead antibodies both match with the target antigens;
after determining that the antigens to be detected have been bound with the magnetic bead antibodies and the substrate antibodies, applying a first magnetic field to the detection chamber to enable the biological magnetic beads to move toward a side wall, where a detection member is disposed, of the detection chamber; and
according to an electrical signal output by the detection member while adsorbing the biological magnetic beads, determining information of the antigens.

Optionally, the step of adding biological magnetic beads and liquid including antigens to be detected to a detection chamber includes the steps of:
adding the liquid including the antigens to be detected to the detection chamber; and
after determining that the antigens have been bound with the substrate antibodies of the substrate, adding the biological magnetic beads to the detection chamber.

Optionally, the step of after determining that the antigens have been bound with the substrate antibodies of the substrate, adding the biological magnetic beads to the detection chamber, includes the step of:
after a first length of time after adding the liquid including the antigens to be detected, adding the biological magnetic beads to the detection chamber.

Optionally, the step of adding the biological magnetic beads to the detection chamber includes the step of:
adding a first quantity of the biological magnetic beads to the detection chamber, where the first quantity is greater than the number of the antigens.

Optionally, the detection member is located on the cover plate of the detection chamber and the first magnetic field is a magnetic field that enables the biological magnetic beads to move toward the cover plate of the detection chamber;
after determining that the antigens have been bound with the magnetic bead antibodies and the substrate antibodies and before applying the first magnetic field to the detection chamber, the using method further includes the step of:
applying a second magnetic field to the detection chamber, where the second magnetic field is a magnetic field with a strength for adsorbing the biological magnetic beads which are not bound with the antigens, the first magnetic field is a magnetic field with a strength for adsorbing a chain structure which is a structure combining the substrate antibodies of the substrate, the antigens and the biological magnetic beads, to the detection member, and the strength of the second magnetic field is smaller than the strength of the first magnetic field.

Optionally, the step of according to an electrical signal output by the detection member while adsorbing the biological magnetic beads, determining information of the antigens includes the steps of:

after applying the second magnetic field to the detection chamber, obtaining a first electrical signal output by the detection member;

after applying the first magnetic field to the detection chamber, obtaining a second electrical signal output by the detection member; and according to the first electrical signal and the second electrical signal output by the detection member, determining information of the antigens.

Optionally, the detection member is a piezoresistive film layer; and the step of according to the first electrical signal and the second electrical signal output by the detection member, determining information of the antigens includes the steps of:

according to a first resistivity and a second resistivity output by the detection member, determining a resistivity difference; and according to the corresponding relationship between a prestored resistivity difference with the number of target antigens, determining the number of the antigens to be detected.

Optionally, the detection member is a piezoelectric film layer; and the step of according to the first electrical signal and the second electrical signal output by the detection member, determining information of the antigens includes the steps of:

according to a first voltage value and a second voltage value output by the detection member, determining a voltage difference; and according to the corresponding relationship between a prestored voltage difference with the number of target antigens, determining the number of the antigens to be detected.

Optionally, the detection member is a quartz crystal microbalance; and the step of according to the first electrical signal and the second electrical signal output by the detection member, determining information of the antigens includes the steps of:

according to a first vibration frequency and a second vibration frequency output by the detection member, determining a frequency difference; and according to the corresponding relationship between a prestored frequency difference with the number of target antigens, determining the number of the antigens to be detected.

Optionally, the detection member is located on the substrate of the detection chamber and the first magnetic field is a magnetic field that enables the biological magnetic beads to move toward to the substrate of the detection chamber;

after determining that the antigens have been bound with the magnetic bead antibodies and the substrate antibodies and before applying the first magnetic field to the detection chamber, the using method further includes the step of:

removing the biological magnetic beads which are not bound with the antigens in the detection chamber.

Optionally, the step of removing the biological magnetic beads which are not bound with the antigens in the detection chamber includes the step of:

removing the biological magnetic beads which are not bound with the antigens to be detected in the detection chamber, through solution flushing or magnetic field driving.

DETAILED DESCRIPTION OF THE EMBODIMENTS

In order to make the objectives, technical solution and advantages of the disclosure clearer, accompanying drawings will be incorporated below to describe specific embodiments of an immunodetection chip and an immunodetection method provided by embodiments of the disclosure in details. It should be understood that the preferred embodiments described below are only for describing and interpreting the disclosure, but not to define the disclosure. Moreover, in a case of no inconsistency, embodiments in the disclosure and features of embodiments can be combined to one another. It should be noted that the size and shape of each drawing among accompanying drawings do not reflect a true scale, as they just aim to illustrate contents of the disclosure. Further, a same or similar reference marker from the beginning to the end represents a same or similar element or an element having a same or similar function.

Immunofluorescence technique and chemiluminescence immunoassay analyze a detected substance by detecting an optical signal of a luminescent substance, which need higher requirements on an optical device. Therefore, the detection cost is high. For radio immunoassay technique, due to radioactive pollution of isotopes, special detection device and certain protection conditions are required. Therefore, there are many limits for this detection method. What is more, general immunodetection methods need to separate antigens participating in a reaction, which leads to a detection result being greatly influenced by a separation result, thus a required accuracy is often difficult to reach.

Figure 1:
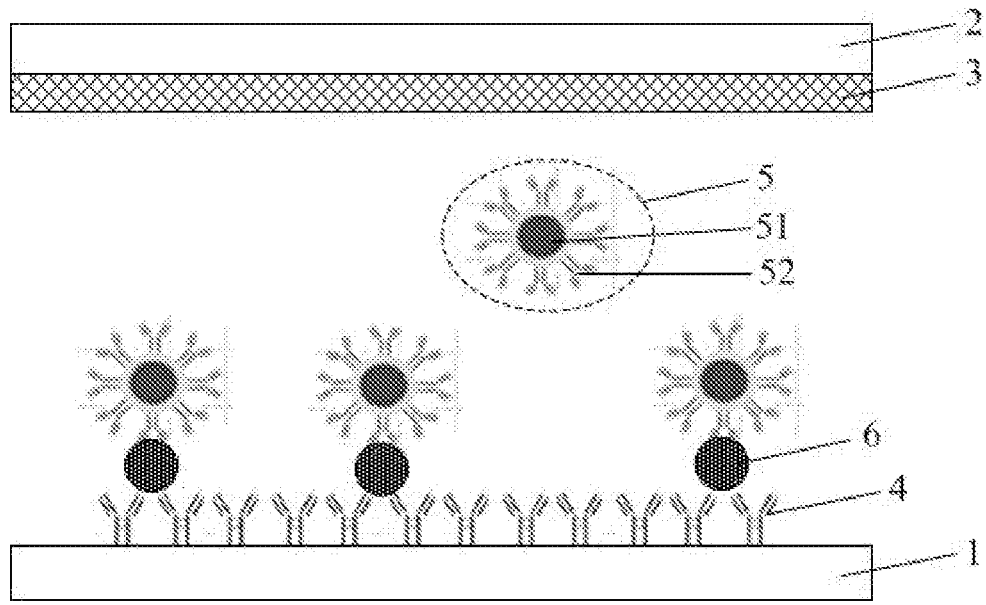
FIG. 1 is a schematic diagram illustrating detection of an immunodetection chip with a detection member being located on a cover plate, provided by an embodiment of the disclosure.

An embodiment of the disclosure provides an immunodetection chip. Referring to FIG. 1, the immunodetection chip includes:

a substrate 1, and a cover plate 2;

wherein the substrate 1 is disposed opposite to the cover plate 2, thereby forming a detection chamber; one side, facing the cover plate 2, of the substrate 1 is fixedly provided with substrate antibodies 4, and an inside wall of the detection chamber is provided with a detection member 3, the detection member 3 is configured to output a corresponding electrical signal while adsorbing biological magnetic beads; and the substrate antibodies 4 match with target antigens.

In the embodiment of the disclosure, an immunodetection chip includes a substrate 1 and a cover plate 2 disposed opposite to each other, and a detection member 3 located on a side wall of a detection chamber. Further, by adding biological magnetic beads 5 and antigens 6 to the detection chamber firstly, if the antigens 6 are the target antigens, the antigens 6 can be bound with substrate antibodies 4 of the substrate 1 in the detection chamber and magnetic bead antibodies 52 of biological magnetic beads 5 to form an integral structure. Then, a second magnetic field is applied to the detection chamber. Since the biological magnetic beads 5 can move under the effect of magnetic field, the biological magnetic beads 5 bound with antigens 6 can be made to move toward a side wall with the detection member 3 is provided, of the detection chamber. When the detection member 3 detects a structural attachment including biological magnetic beads 5, a change in a corresponding signal is generated, such that information of antigens 6 in a sample to be detected can be determined according to a signal output by the detection member 3. Furthermore, a costly optical detection instrument upon immunodetection with an optical signal is not needed, and the problem of strict protection restrictions upon detection with elements including radioactive elements can also be avoided. What is more, the number of antigens in liquid to be detected can be quantitatively detected. As compared with the prior art, by which detection of antigens is influenced by a separation result, since before a reaction of antibodies and antigens it is required to separate antigens from a sample liquid in which antigens originally exist, the disclosure does not need a step for separating antigens, such that no influence of a separation result will be suffered, resulting in high detection accuracy.

It should be noted that FIG. 1 is a schematic diagram for illustrating binding of antigens 6 with substrate antibodies 4 of a substrate 1 and magnetic bead antibodies 52 of biological magnetic beads 5, aiming to understand acting principles of an immunodetection chip of an embodiment of the disclosure more clearly. In a specific implementation, concerning the structure of the immunodetection chip itself, the chip may not include antigens 6 and biological magnetic beads 5. Biological magnetic beads 5 can specifically include magnetic beads 51 and antibodies 52 enveloping the magnetic beads 51.

In a specific implementation, the substrate 1 can be made of glass, silicon or polydimethylsiloxane (PDMS). The substrate antibodies 4 of the substrate 1 can be fixed to the substrate through an embedding method and a gold film surface self-assembly method.

In a specific implementation, as shown in FIG. 1, in the embodiment of the disclosure, the detection member 3 is located on one side, facing the substrate 1, of the cover plate 2. In the embodiment of the disclosure, when the detection member 3 is located on the cover plate 2 of the detection chamber, upon detection through the immunodetection chip, biological magnetic beads 5 remaining in the detection chamber which are not bound can be further adsorbed to the detection member by firstly applying a second magnetic field. Then, by applying a first magnetic field, a chain structure including biological magnetic beads-antigens-substrate antibodies can further depart from restraining of the substrate 1 and can also be adsorbed to the detection member 3 of the cover plate 2. By applying a magnetic field twice, influence of biological magnetic beads 5 which are not bound can be further removed, so as to obtain the number of antigens 6 bound with biological magnetic beads 5.

Figure 2:
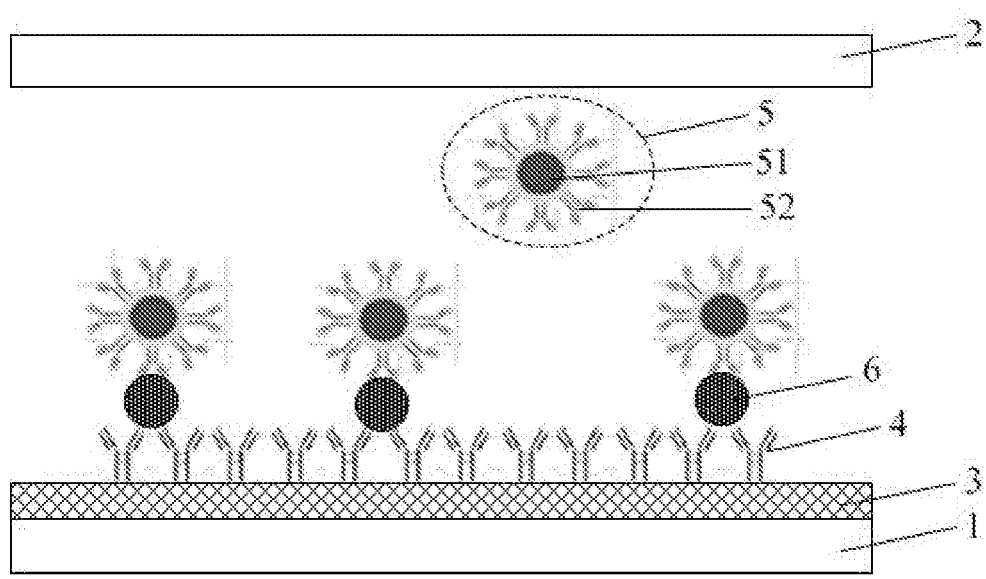
FIG. 2 is a schematic diagram illustrating detection of an immunodetection chip with a detection member being located on a substrate, provided by an embodiment of the disclosure.

In a specific implementation, as shown in FIG. 2, in the embodiment of the disclosure, the detection member 3 is located between the substrate antibodies 4 and the substrate 1. In the embodiment of the disclosure, when the detection member 3 is located on the substrate 1 of the detection chamber, upon detection through the immunodetection chip, biological magnetic beads 5 which are not bound with antigens in the detection chamber can be firstly removed before the second magnetic field is applied to the detection chamber, such that the problem of detection of the number of antigens being influenced due to the detection member 3 adsorbing biological magnetic beads 5 which are not bound with the antigens can be avoided.

Figure 3:
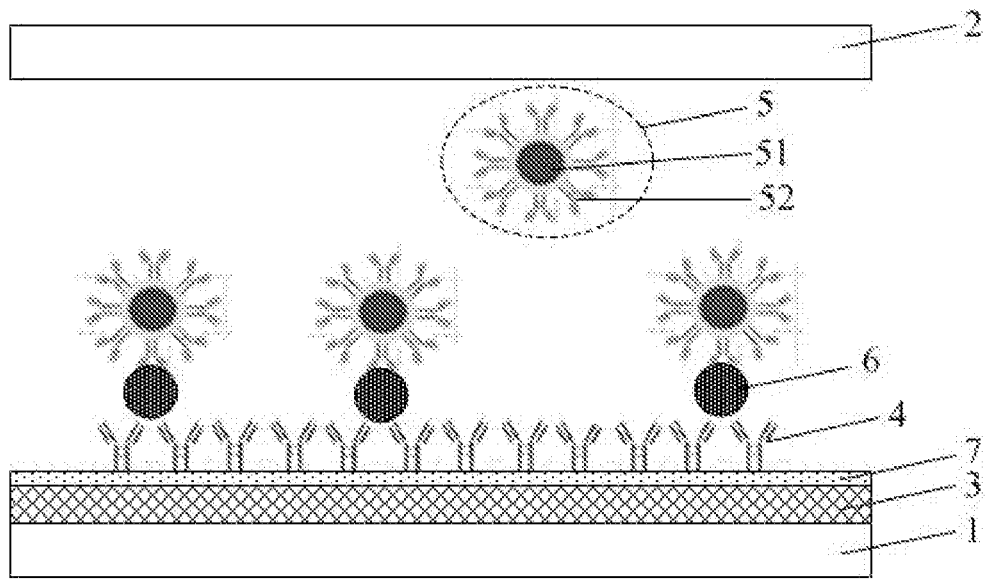
FIG. 3 is a schematic diagram illustrating detection of an immunodetection chip including a biological modification layer, provided by an embodiment of the disclosure.

In a specific implementation, as shown in FIG. 3, in the embodiment of the disclosure, a biological modification layer 7 is further disposed between the substrate antibodies 4 and the detection member 3. The biological modification layer 7 can specifically be a nanogold film layer or a high molecular polymer organic film layer. The high molecular polymer organic film layer can specifically be made of phthalate diethylene glycol diacrylate. In the embodiment of the disclosure, the detection member 3 is firstly disposed on the substrate 1, the biological modification layer 7 is disposed on the detection member 3, and the substrate antibodies 4 are disposed on the biological modification layer 7. The biological modification layer 7 can effectively facilitate to fix the substrate antibodies 4 to the detection member 3, i.e. for example, when the biological modification layer 7 is a gold film layer, the gold film layer can be firstly formed on the substrate 1; afterward, the substrate antibodies 4 are formed on the gold film layer. Due to high chemical activity of nanogold, it can effectively adsorb the substrate antibodies 4, such that the substrate antibodies 4 can be made to be fixed to the substrate 1. When the biological modification layer 7 is made of phthalate diethylene glycol diacrylate, upon manufacturing, the substrate antibodies 4 can be mixed with phthalate diethylene glycol diacrylate in a solution state, and the substrate 1 is coated with the mixture through a coating manner, such that fixing of the substrate antibodies 4 to the substrate 1 can also be realized.

In a specific implementation, in the embodiment of the disclosure, the detection member 3 can specifically be a quartz crystal microbalance, a piezoelectric film layer or a piezoresistive film layer. The piezoelectric film layer can specifically be made of aluminium nitride, zinc oxide, lead zirconate titanate or polyvinylidene fluoride. The piezoresistive film layer can specifically be made of silicon carbide, tantalum nitride, carbon nanotubes or polysilicon.

Based on the same inventive concept, the embodiment of the disclosure further provides an immunodetection device, where the immunodetection device includes the immunodetection chip provided by the embodiment of the disclosure.

In a specific implementation, by combining with FIG. 3, in the embodiment of the disclosure, the immunodetection device further includes: biological magnetic beads 5; where the biological magnetic beads 5 include magnetic beads 51, and magnetic bead antibodies 52 enveloping the magnetic beads 51, and the biological magnetic beads 5 are added to the detection chamber of the immunodetection chip to bind with antigens 6 while being used to detect antigens.

Figure 4:
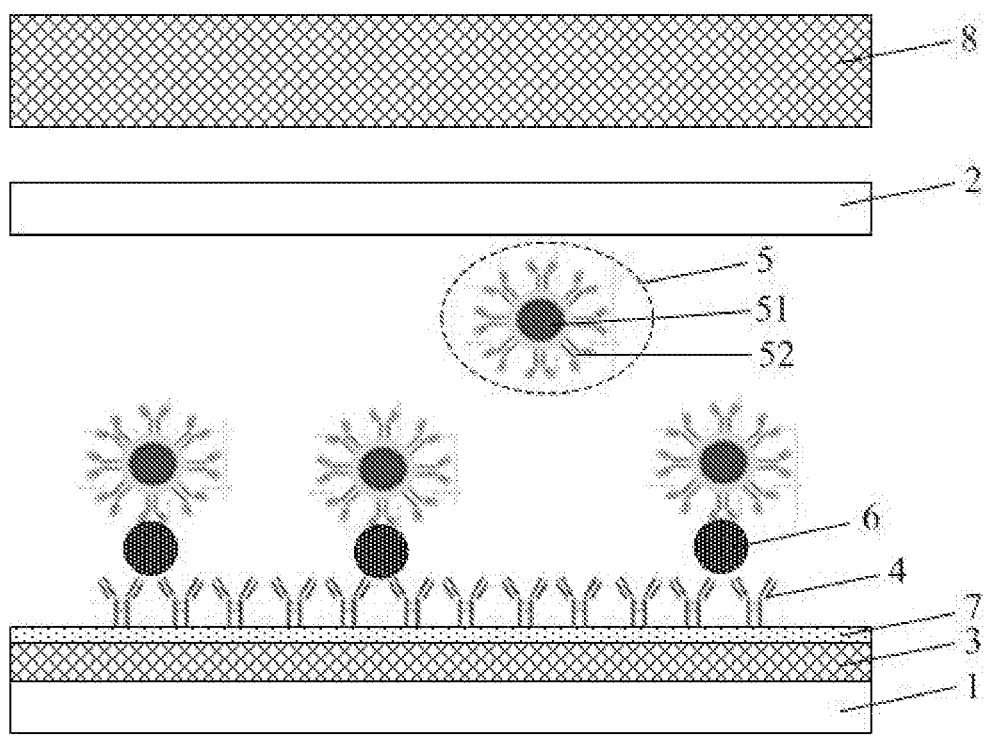
FIG. 4 is a schematic diagram illustrating a magnetic field generation member being at one side of a cover plate, facing away from a substrate, provided by an embodiment of the disclosure.

In a specific implementation, referring to FIG. 4, in the embodiment of the disclosure, the immunodetection device further includes a magnetic field generation member 8 that applies a magnetic field to the immunodetection chip while being used to detect antigens 6.

Figure 5:
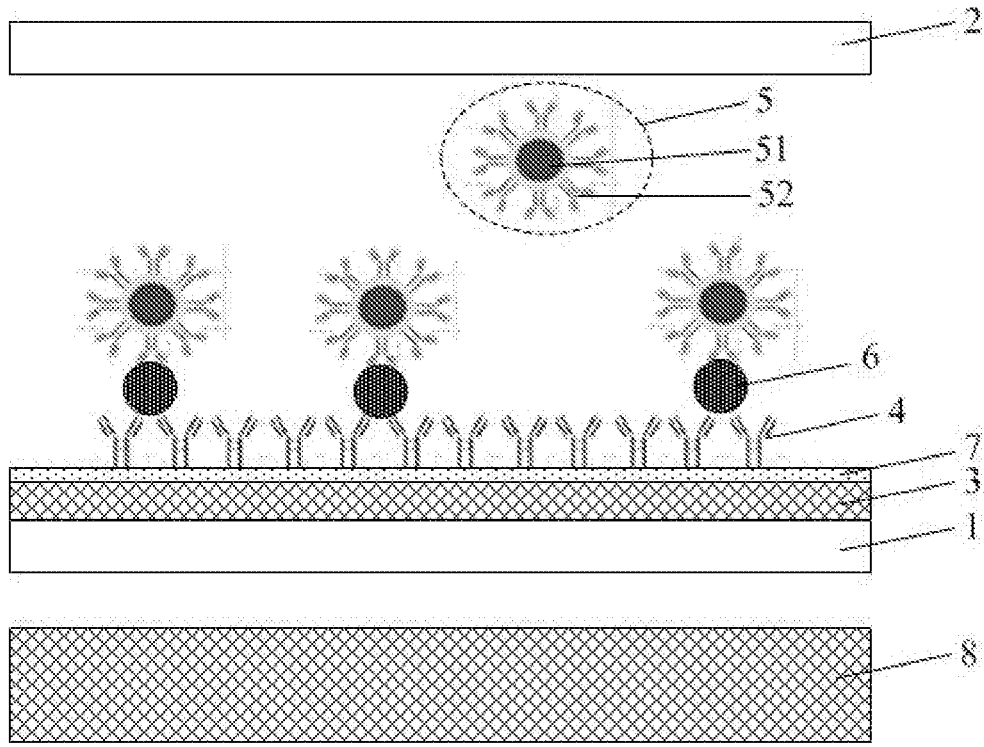
FIG. 5 is a schematic diagram illustrating a magnetic field generation member being at one side of a substrate, facing away from a cover plate, provided by an embodiment of the disclosure.

Of course, the above is just described with locating of the magnetic field generation member 8 at one side, facing away from a substrate 1, of a cover plate 2 as an example. In a specific implementation, referring to FIG. 5, the magnetic field generation member 8 is located on one side, facing away from a cover plate 2, of a substrate 1.

Figure 6:
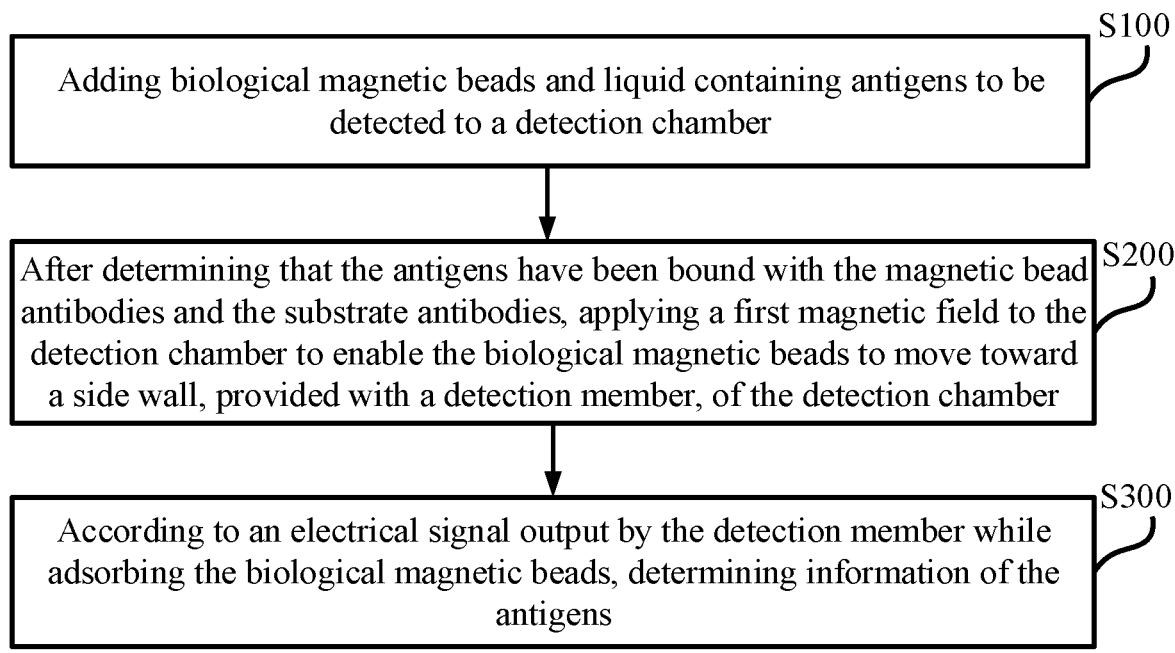
FIG. 6 is a flow diagram of an immunodetection method provided by an embodiment of the disclosure.

Based on the same inventive concept, the embodiment of the disclosure further provides a using method of the immunodetection chip provided by the embodiment of the disclosure. As shown in FIG. 6, the using method includes the steps of:

step S100, adding biological magnetic beads and liquid including antigens to be detected to a detection chamber, where the biological magnetic beads include magnetic beads and magnetic bead antibodies enveloping the magnetic beads and matching with the target antigens, a substrate of the detection chamber is fixedly provided with substrate antibodies, and the substrate antibodies and the magnetic bead antibodies are the same to facilitate specific binding with the same type of antigens;

step S200, after determining that the antigens have been bound with the substrate antibodies and the magnetic bead antibodies, applying a first magnetic field to the detection chamber to enable the biological magnetic beads to move toward a side wall with a detection member being provided, of the detection chamber; and step S300, according to an electrical signal output by the detection member while adsorbing the biological magnetic beads, determining information of the antigens. Information of the antigens can specifically be types of the antigens and can also be the number of the antigens. That is, for example, when the substrate is provided with substrate antibodies corresponding to flu virus antigens, it can be detected whether liquid to be detected contains flu virus antigens or not.

The immunodetection method provided by the embodiment of the disclosure can, by adding biological magnetic beads and antigens to the detection chamber firstly, make the antigens be bound with substrate antibodies of the substrate in the detection chamber and antibodies of biological magnetic beads into an integral structure. Then, a first magnetic field is applied to the detection chamber. Since the biological magnetic beads can move under the effect of the magnetic field, further the biological magnetic beads bound with the antigens can be made to move toward a side wall, where the detection member is disposed, of the detection chamber. When the detection member detects a structural attachment including the biological magnetic beads, a change in a corresponding signal is generated, such that according to a signal output by the detection member, information of the antigens in a sample to be detected can be determined. Furthermore, the problem of needing a costly optical detection instrument upon immunodetection with an optical signal can be avoided, and the problem of strict protection restrictions upon detection with elements including radioactive elements can also be avoided. What is more, the number of antigens in the liquid to be detected can be quantitatively detected. As compared with the prior art, by which detection of antigens is influenced by a separation result, since before a reaction of antibodies and antigens it is required to separate antigens from a sample liquid in which antigens originally exist, the disclosure does not need a step for separating antigens, such that no influence of a separation result will be suffered, resulting in high detection accuracy.

In a specific implementation, the magnetic bead antibodies and the substrate antibodies in the embodiment of the disclosure can specifically be corresponding antibodies for detecting e.g. rabies virus antigens, and can also be corresponding antibodies for detecting flu virus antigens or other type of antibodies. Antigens can specifically be bound with two or more substrate antibodies or magnetic bead antibodies.

Figure 7:
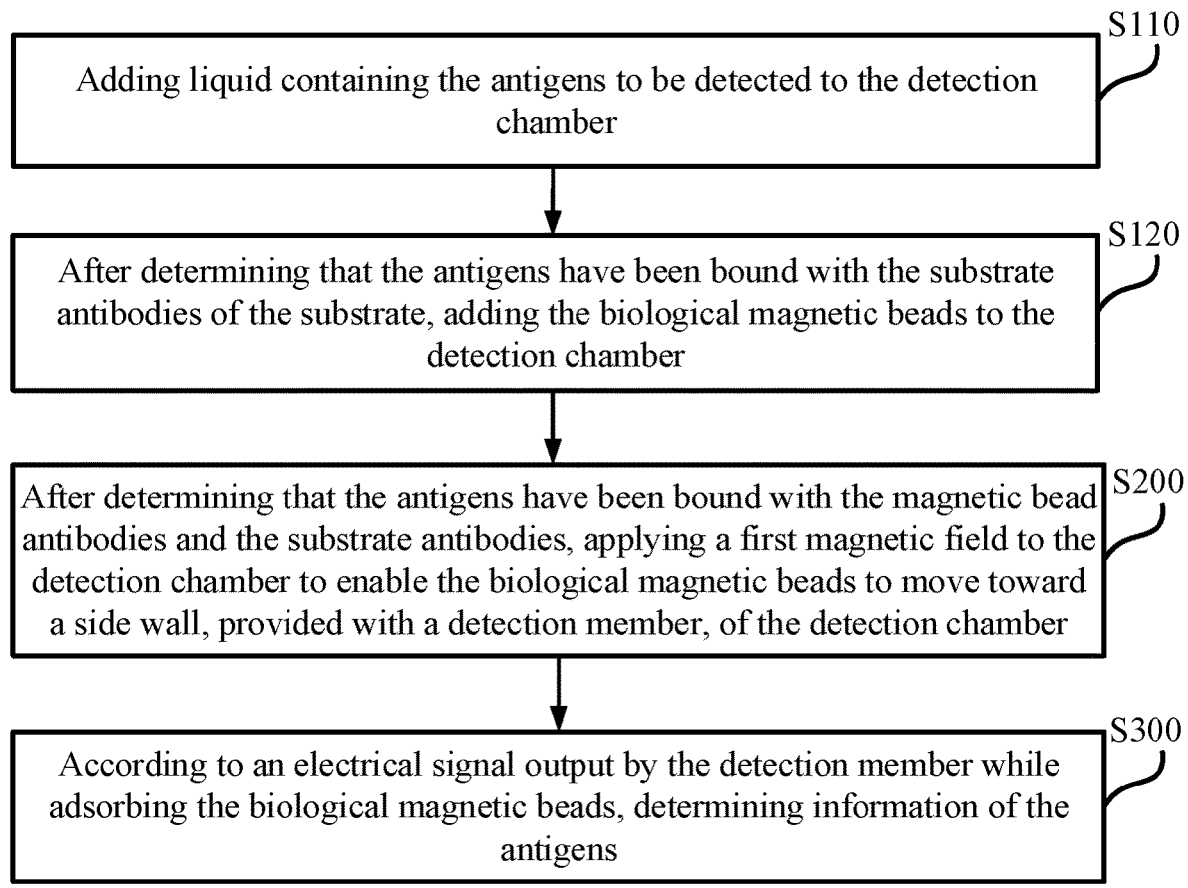
FIG. 7 is a flow diagram of a specific immunodetection method provided by an embodiment of the disclosure.

In a specific implementation, upon adding the biological magnetic beads and the antigens, if the biological magnetic beads are firstly added and the antigens are added next, the antigens in liquid to be detected are likely to be only bound with the antibodies of the biological magnetic beads, rather than bound with the substrate antibodies of the substrate. Therefore, in the embodiment of the disclosure, referring to FIG. 7, the step S100 of adding biological magnetic beads and liquid including antigens to be detected to a detection chamber includes the steps of:

step S110, adding the liquid including the antigens to be detected to the detection chamber; and step S120, after determining that the antigens have been bound with the substrate antibodies of the substrate, adding the biological magnetic beads to the detection chamber.

In the embodiment of the disclosure, by adding the antigens to be detected to the detection chamber firstly and adding the biological magnetic beads next, one ends of the antigens to be detected can be made to be firstly bound with the substrate antibodies of the substrate in the detection chamber. When the biological magnetic beads are added next, the other ends of the antigens to be detected can be bound with the magnetic bead antibodies of the biological magnetic beads, such that a chain structure including biological magnetic beads-antigens-substrate antibodies can be formed. Furthermore, upon applying a magnetic field in a later stage, the number of the antigens to be detected can be reflected through the amount of the chain structures adsorbed to the substrate. Of course, the antigens are of less possibility of all binding with the antibodies of the biological magnetic beads. If a higher detection accuracy is not required, the biological magnetic beads can also be firstly added and the antigens are added next, or the biological magnetic beads and the antigens are simultaneously added to the detection chamber. In addition, it should be understood that when the step S100 includes the steps of firstly adding the antigens and then adding the biological magnetic beads, the corresponding step S200 of determining that the antigens have been bound with the magnetic bead antibodies and the substrate antibodies can specifically be understood as determining that the antigens have been bound with the magnetic bead antibodies of the biological magnetic beads, i.e. in the detection process, the antigens are firstly bound with the substrate antibodies of the substrate and then bound with the magnetic bead antibodies of the biological magnetic beads.

It should be noted that, for the substrate antibodies disposed at the substrate in the embodiment of the disclosure, on one hand, since the antigens are detected through the detection chamber of the detection chip, which is generally a process of detecting the antigens in a liquid flow process, the substrate antibodies disposed at the substrate of the detection chamber can timely capture the antigens when the antigens to be detected flow through a reaction activity area of the detection chamber, so as to avoid the antigens from being directly flowing out of the detection chamber without participating in the reaction while the liquid is in the flow process. On the other hand, if the detection chamber is only provided with a liquid inlet but without a liquid outlet, the detection process is a process of detecting the antigens not in the liquid flow process. The substrate antibodies of the substrate in the embodiment of the disclosure can distinguish the biological magnetic beads participating in the reaction from the biological magnetic beads without participating in the reaction, such that by applying the magnetic field of different strengths twice, i.e. by applying the magnetic field for the first time, the detection member only adsorbs the biological magnetic beads without participating in the reaction and the biological magnetic beads participating in the reaction are fixed to the substrate in a structure of biological magnetic beads-antigens-substrate antibodies. Upon applying the magnetic field for the second time, the structure of biological magnetic beads-antigens-substrate antibodies which is originally fixed to the substrate can also be adsorbed to the detection member, such that through the detection result of the detection member under the two magnetic fields, influence of the biological magnetic beads without participating in the reaction on the detection member can be removed. Further, influence of the biological magnetic beads without participating in the reaction on detection of the number of the antigens can be avoided. If the substrate is not provided with the substrate antibodies, in the process of applying the magnetic field twice, the biological magnetic beads participating in the reaction are adsorbed to the detection member together with the biological magnetic beads without participating in the reaction, such that the number of the biological magnetic beads participating in the reaction cannot be reflected, thus further influencing the detection result of the number of the antigens.

In a specific implementation, in the embodiment of the disclosure, the step S120 of after determining that the antigens have been bound with the substrate antibodies of the substrate, adding the biological magnetic beads to the detection chamber can specifically include the step of: after a first length of time after adding the liquid including the antigens to be detected, adding the biological magnetic beads to the detection chamber. The first length of time can specifically be the time required for complete reaction of the antigens with the substrate antibodies of the substrate.

In a specific implementation, in the embodiment of the disclosure, the step S120 of adding the biological magnetic beads to the detection chamber can specifically include the step of: adding a first quantity of biological magnetic beads to a detection chamber, where the first quantity is greater than the number of antigens. In the embodiment of the disclosure, adding a first quantity of biological magnetic beads to a detection chamber, where the first quantity is greater than the number of antigens, can ensure complete participation of antigens in the reaction, so as to obtain the number of antigens in liquid to be detected accurately.

In a specific implementation, the detection member in the embodiment of the disclosure can specifically include a substrate and a cover plate disposed opposite to each other, and the substrate and the cover plate form a detection chamber. The detection chamber can only be provided with a liquid inlet, and can also be provided with both a liquid inlet and a liquid outlet. The detection member can specifically be disposed at the substrate of the detection chamber and can also be disposed at the cover plate of the detection chamber. Description is made as follows on related steps of the immunodetection method of the embodiment of the disclosure according to specific different disposing positions of the detection member.

For example, in the embodiment of the disclosure, the detection member is located on the cover plate of the detection chamber and the first magnetic field is a magnetic field that enables biological magnetic beads to move toward the cover plate of the detection chamber, thus before the step S200, i.e. after determining that the antigens have been bound with the magnetic bead antibodies and the substrate antibodies and before applying the first magnetic field to a detection chamber, the using method can further include the step of: applying a second magnetic field to the detection chamber, where the second magnetic field is a magnetic field with a strength only for adsorbing the biological magnetic beads which are not bound with the antigens, the first magnetic field is a magnetic field with a strength for adsorbing a chain structure which is a structure combining the substrate antibodies of the substrate, the antigens and the biological magnetic beads, to the detection member, and the strength of the second magnetic field is smaller than the strength of the first magnetic field. In the embodiment of the disclosure, when the detection member is located on the cover plate of the detection chamber, the biological magnetic beads remaining in the detection chamber which are not bound can be further adsorbed to the detection member by firstly applying a second magnetic field. For the chain structure of biological magnetic beads-antigens-substrate antibodies combined with the substrate, due to the fixing effect of the substrate to the substrate antibodies, when the strength of the magnetic field is not strong enough, the chain structure is still fixed to the substrate. By then applying a first magnetic field, the chain structure including biological magnetic beads-antigens-substrate antibodies can further depart from restraining of the substrate and can also be adsorbed to the detection member of the cover plate. By applying the magnetic field twice, influence of the biological magnetic beads which are not bound can be further removed, so as to obtain the number of the antigens bound with the biological magnetic beads.

Correspondingly, when the applied magnetic field is a second magnetic field and a first magnetic field with the strength increased in order, in the embodiment of the disclosure, the step S300 of according to an electrical signal output by the detection member while adsorbing the biological magnetic beads, determining information of the antigens, can specifically include the steps of:

step S310, after applying the second magnetic field to the detection chamber, obtaining a first electrical signal output by the detection member;

step S320, after applying the first magnetic field to the detection chamber, obtaining a second electrical signal output by the detection member; and step S330, determining information of the antigens, according to the first electrical signal and the second electrical signal output by the detection member.

Correspondingly, when the detection member is a piezoresistive film layer, the step S330 of according to the first electrical signal and the second electrical signal output by the detection member, determining information of the antigens, can specifically include the steps of:

step S3311, according to a first resistivity and a second resistivity output by the detection member, determining a resistivity difference; and step S3312, according to the corresponding relationship between a prestored resistivity difference with the number of target antigens, determining the number of the antigens to be detected. That is, by applying the magnetic field of different strengths twice, i.e. during applying the magnetic field for the first time, only the biological magnetic beads without participating in the reaction move to the detection member under the effect of the second magnetic field, and the biological magnetic beads participating in the reaction are fixed to the substrate in a structure of biological magnetic beads-antigens-substrate antibodies. Upon applying the magnetic field for the second time, the structure of biological magnetic beads-antigens-substrate antibodies which is originally fixed to the substrate can also move to the detection member, such that through the detection result of the detection member in the two magnetic fields, influence of the biological magnetic beads without participating in the reaction on the detection member can be removed; that is, the generation of a resistivity difference is caused by the biological magnetic beads participating in the reaction, i.e. by the chain structure of biological magnetic beads-antigens-substrate antibodies. That is, the resistivity difference is in a direct proportion correlation with the number of the chain structures. Since biological magnetic beads form a chain structure with antigens and antibodies, i.e. the number of antigens is in a corresponding relationship with the number of chain structures (for example, one chain structure includes one antigen correspondingly), the number of antigens is also in a direct proportion correlation with a resistivity difference, i.e. the larger the resistivity difference, the more the number of antigens.

Correspondingly, when the detection member is a piezoelectric film layer, in the embodiment of the disclosure, the step S330 of according to the first electrical signal and the second electrical signal output by the detection member, determining information of the antigen, includes the steps of:

step S3321, according to a first voltage value and a second voltage value output by the detection member, determining a voltage difference; and step S3322, according to the corresponding relationship between a prestored voltage difference with the number of target antigens, determining the number of the antigens to be detected. Similarly, by applying the magnetic field of different strengths twice, i.e. during applying the magnetic field for the first time, only the biological magnetic beads without participating in the reaction move to the detection member under the effect of the second magnetic field, and the biological magnetic beads participating in the reaction are fixed to the substrate in a structure of biological magnetic beads-antigens-substrate antibodies. Upon applying the magnetic field for the second time, the structure of biological magnetic beads-antigens-substrate antibodies which is originally fixed to the substrate can also be adsorbed to the detection member, such that through the detection result of the detection member in the two magnetic fields, influence of the biological magnetic beads without participating in the reaction on the detection member can be removed; i.e. the generation of a voltage difference is caused by the biological magnetic beads participating in the reaction, i.e. by the chain structure of biological magnetic beads-antigens-substrate antibodies. That is, the voltage difference is in a direct proportion correlation with the number of the chain structures. Since biological magnetic beads form a chain structure with antigens and antibodies, i.e. the number of antigens is in a corresponding relationship with the number of chain structures (for example, one chain structure includes one antigen correspondingly), the number of antigens is also in a direct proportion correlation with a voltage difference, i.e. the larger the voltage difference, the more the number of antigens.

Correspondingly, when the detection member is a quartz crystal microbalance, in the embodiment of the disclosure, the step S330 of according to the first electrical signal and the second electrical signal output by the detection member, determining information of the antigens, includes the steps of:

step S3331, according to a first vibration frequency and a second vibration frequency output by the detection member, determining a frequency difference; and step S3332, according to the corresponding relationship between a prestored frequency difference with the number of target antigens, determining the number of the antigens to be detected. Similarly, by applying the magnetic field of different strengths twice, i.e. during applying the magnetic field for the first time, the detection member adsorbs only biological magnetic beads without participating in the reaction, and the biological magnetic beads participating in the reaction are fixed to the substrate in a structure of biological magnetic beads-antigens-substrate antibodies. Upon applying the magnetic field for the second time, the structure of biological magnetic beads-antigens-substrate antibodies which is originally fixed to the substrate are also be adsorbed to the detection member, such that through the detection result of the detection member in the two magnetic fields, influence of the biological magnetic beads without participating in the reaction on the detection member can be removed; i.e. the generation of a frequency difference is caused by the biological magnetic beads participating in the reaction, i.e. by the chain structure of biological magnetic beads-antigens-substrate antibodies. That is, the frequency difference is in a direct proportion correlation with the number of the chain structures. Since biological magnetic beads form a chain structure with antigens and antibodies, i.e. the number of antigens is in a corresponding relationship with the number of the chain structures (for example, one chain structure includes one antigen correspondingly), the number of antigens is also in a direct proportion correlation with a frequency difference, i.e. the larger the frequency difference, the more the number of antigens.

Figure 8:
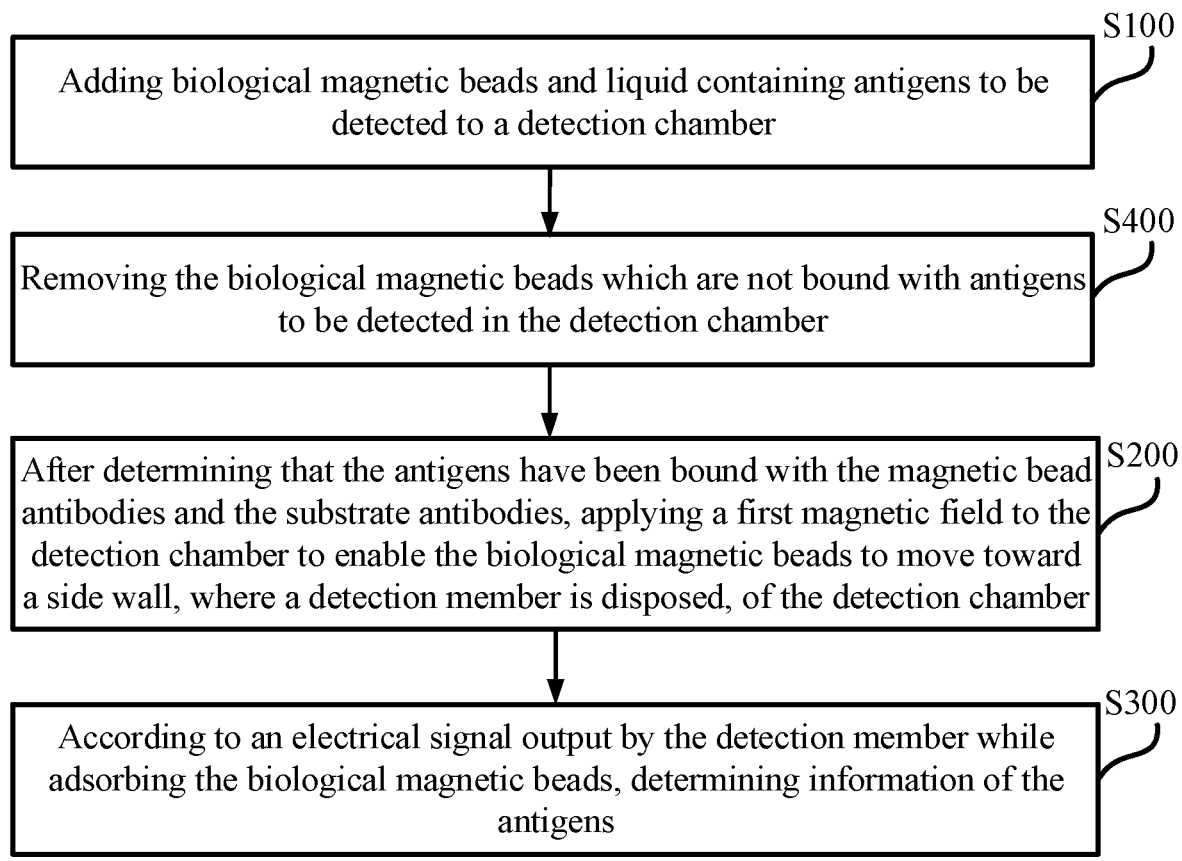
FIG. 8 is a flow diagram of an immunodetection method upon locating of a detection member at a substrate, provided by an embodiment of the disclosure.

For example again, in the embodiment of the disclosure, when the detection member is located on the substrate of the detection chamber and the first magnetic field is a magnetic field that enables the biological magnetic beads to move toward the substrate of the detection chamber, for the step S200 of after determining that the antigens have been bound with the magnetic bead antibodies and the substrate antibodies and before applying the first magnetic field to a detection chamber, referring to FIG. 8, the using method of the embodiment of the disclosure can further include: step S400, removing the biological magnetic beads which are not bound with the antigens in the detection chamber. In the embodiment of the disclosure, when the detection member is located on the substrate of the detection chamber, a chain structure including biological magnetic beads-antigens-substrate antibodies, before and after a magnetic field is applied, is adsorbed to the substrate all the time. Through the magnetic field applied twice with the strength increased in order, influence of biological magnetic beads cannot be avoided. Therefore, when the detection member is located on the substrate of the detection chamber, in the embodiment of the disclosure, the biological magnetic beads which are not bound with antigens in the detection chamber can be removed before a magnetic field is applied to the detection chamber, such that the problem that adsorption of the biological magnetic beads on the detection member influences detection of the number of the antigens can be avoided. It should be understood that when the detection member is located on the substrate of the detection chamber, the direction of a magnetic field that enables the biological magnetic beads to move toward the direction of the detection member needs to satisfy the requirement of enabling the biological magnetic beads to move toward the substrate of the detection chamber. The direction differs from the direction of the magnetic field applied twice when the detection member is located on the cover plate of the detection chamber. When the detection member is located on the cover plate of the detection chamber, the direction of the magnetic field applied twice needs to satisfy the requirement of enabling the biological magnetic beads to move toward the cover plate of the detection chamber.

It should be noted that when the detection chamber is located on the substrate of the detection chamber, only a magnetic field with a constant strength can be applied upon applying a magnetic field to the detection chamber. Since influence of biological magnetic beads has been removed, a signal output by the detection chamber is caused by biological magnetic beads bound with antigens. Furthermore, the number of antigens can also be determined. Specifically, when the detection member is a piezoresistive film layer, a resistivity output by the detection member is caused by a chain structure of biological magnetic beads-antigens-substrate antibodies. That is, the resistivity is in a direct proportion correlation with the number of the chain structures. Since biological magnetic beads form a chain structure with antigens and antibodies, i.e. the number of antigens is in a corresponding relationship with the number of chain structures (for example, one chain structure includes one antigen correspondingly), the number of antigens is also in a direct proportion correlation with a resistivity, i.e. the larger the resistivity, the more the number of antigens.

Specifically, in the embodiment of the disclosure, the step S400 of removing the biological magnetic beads which are not bound with the antigens in the detection chamber, includes the step of: through solution rinsing or magnetic field driving, removing the biological magnetic beads which are not bound with the antigens in the detection chamber. Regarding specific magnetic field driving, the direction in which the biological magnetic beads are made to move by the magnetic field can specifically be a liquid outlet direction of the detection chamber. Solution flushing can specifically be flushing a solution to the liquid inlet of the detection chamber. Since the reacted biological magnetic beads have been fixed to the substrate in a chain structure of biological magnetic beads-antigens-substrate antibodies and the non-reacted biological magnetic beads are in a free state and flow out from the liquid outlet of the detection chamber together with the flushing solution. Regarding magnetic field driving, the acting force generated by the magnetic field can be specifically applied parallel with the substrate and oriented toward the direction of the liquid outlet. Similarly, the reacted biological magnetic beads have been fixed to the substrate in a chain structure of biological magnetic beads-antigens-substrate antibodies and the non-reacted biological magnetic beads are in a free state and move out from the liquid outlet of the detection chamber under the effect of the magnetic field applied toward the liquid outlet direction. Of course, it should be understood that the acting force generated by strength of the magnetic field of removing the non-reacted biological magnetic beads should be smaller than the attaching force of fixing the chain structure of biological magnetic beads-antigens-substrate antibodies to the substrate to avoid discharging biological magnetic beads fixed to the substrate out of the detection chamber as well while the non-reacted biological magnetic beads are removed.

In order to understand the immunodetection method provided by the embodiment of the disclosure more clearly, examples are given below for description through specific embodiments.

Embodiment 1

Embodiment 1 of the disclosure, with a detection member as a quartz crystal microbalance disposed at a cover plate of a detection chamber as an example, describes the immunodetection method of the embodiment of the disclosure.

Figure 9:
FIG. 9 is a schematic diagram upon adding antigens to a detection chip, provided by Embodiment 1 of the disclosure.
Figure 9:
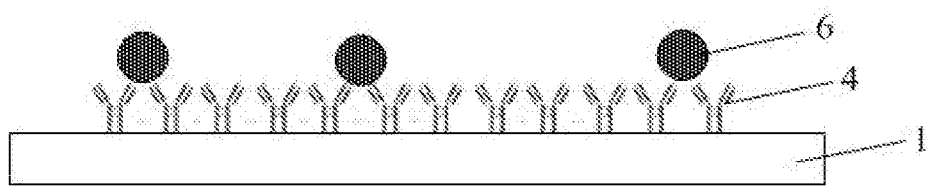

Step 1, adding liquid including the antigens 6 to be detected to the detection chamber, as shown in FIG. 9.

Figure 10:
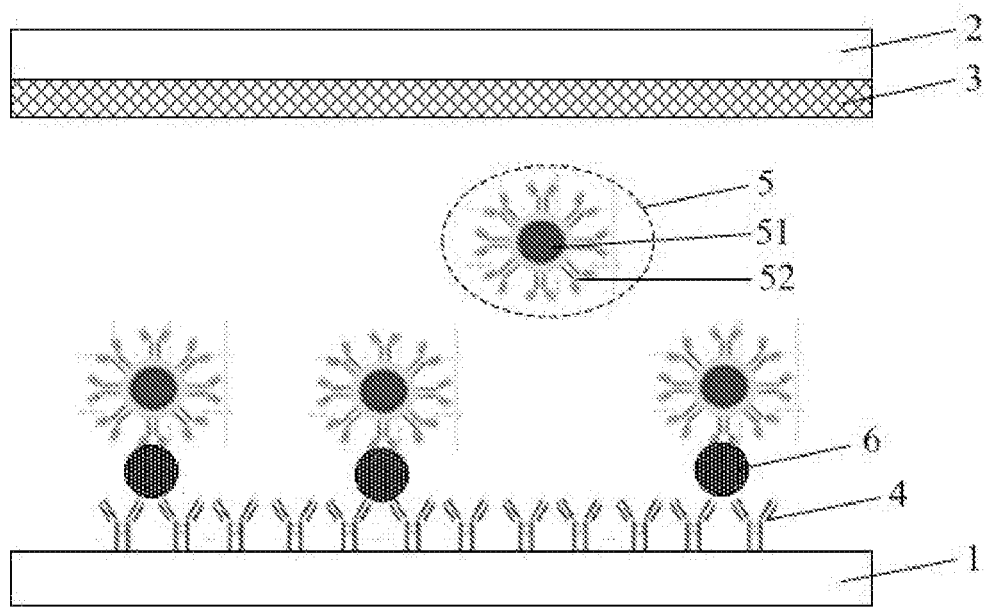
FIG. 10 is a schematic diagram upon adding biological magnetic beads to a detection chip, provided by Embodiment 1 of the disclosure.

Step 2, after a first length of time after adding liquid including antigens 6 to be detected, adding a first quantity of the biological magnetic beads 5 to the detection chamber, as shown in FIG. 10.

Figure 11:
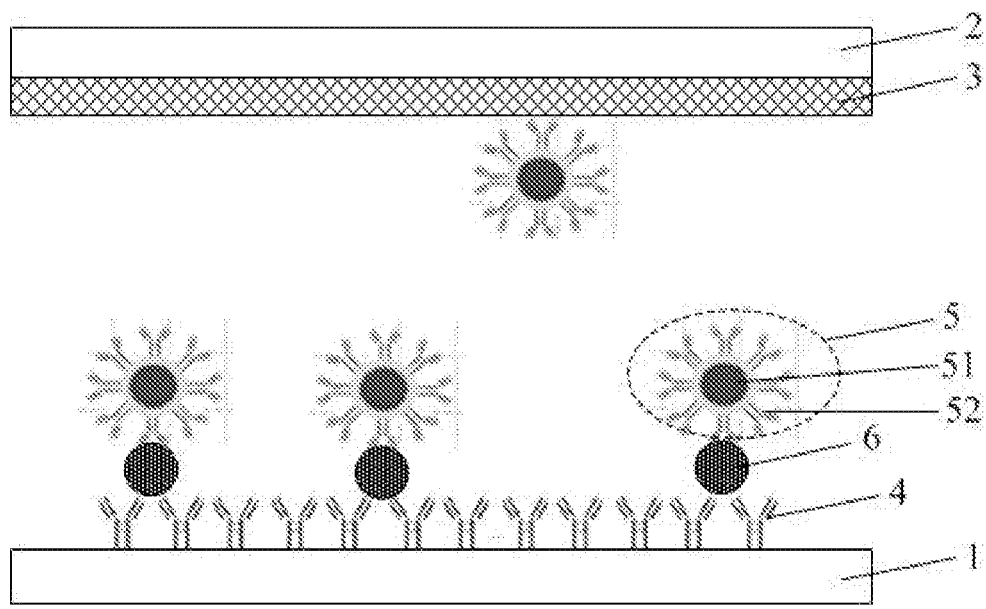
FIG. 11 is a schematic diagram after applying a second magnetic field, provided by Embodiment 1 of the disclosure.

Step 3, applying a second magnetic field to a detection chamber, where the second magnetic field is a magnetic field with a strength only adsorbing biological magnetic beads which are not bound with antigens, as shown in FIG. 11, which is a schematic diagram of a detection chamber after being applied with the second magnetic field.

Step 4, obtaining a first vibration frequency output by a detection chamber 3.

Figure 12:
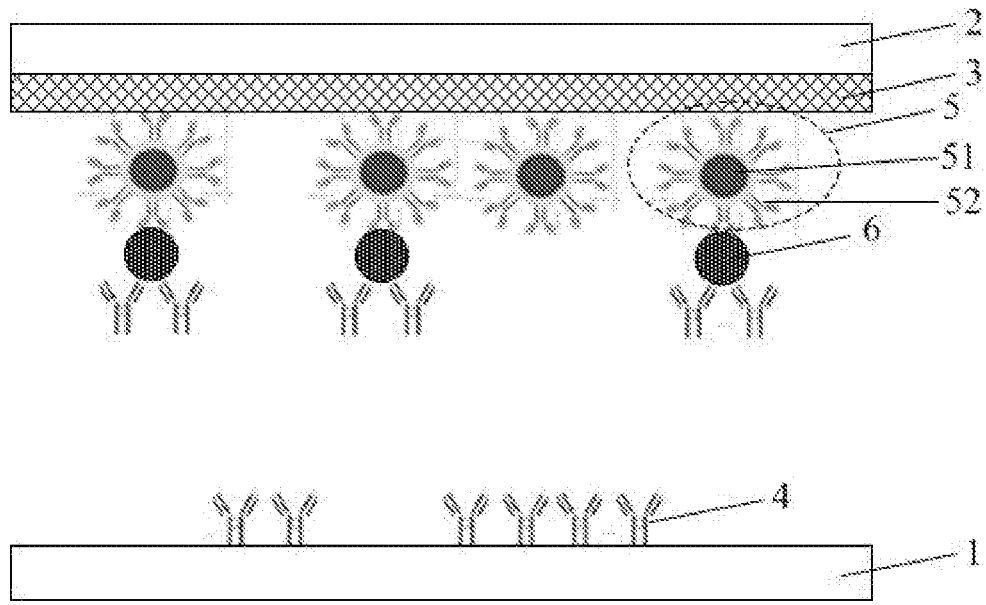
FIG. 12 is a schematic diagram after applying a first magnetic field, provided by Embodiment 1 of the disclosure.

Step 5, applying a first magnetic field to the detection chamber, as shown in FIG. 12, which is a schematic diagram of the detection chamber after being applied with the first magnetic field, where the first magnetic field is a magnetic field with a strength adsorbing a chain structure which is a structure combining substrate antibodies 4 of a substrate 1, antigens and biological magnetic beads, to the detection chamber, and the strength of the second magnetic field is smaller than the strength of the first magnetic field.

Step 6, obtaining a second vibration frequency output by a detection chamber 3.

Step 7, according to the first vibration frequency and the second vibration frequency output by the detection member 3, determining a frequency difference.

Step 8, according to the corresponding relationship between a prestored frequency difference with the number of target antigens, determining the number of the antigens to be detected.

Embodiment 2

Embodiment 2 of the disclosure, with a detection member as a piezoresistive film layer disposed at a substrate of a detection chamber as an example, describes the immunodetection method of the embodiment of the disclosure.

Figure 13:
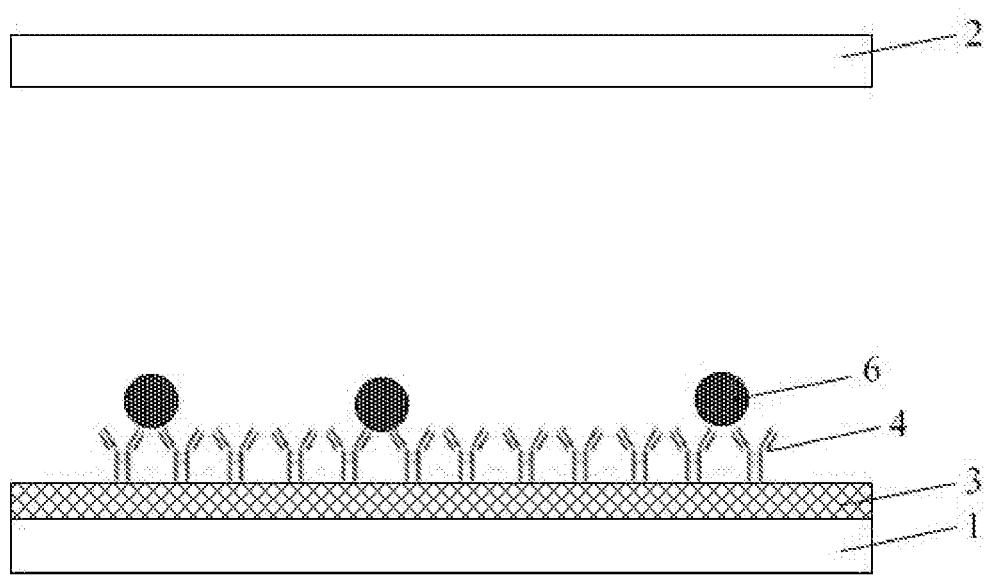
FIG. 13 is a schematic diagram upon adding antigens, provided by Embodiment 2 of the disclosure.

Step 1, adding liquid including the antigens 6 to be detected to the detection chamber, as shown in FIG. 13.

Figure 14:
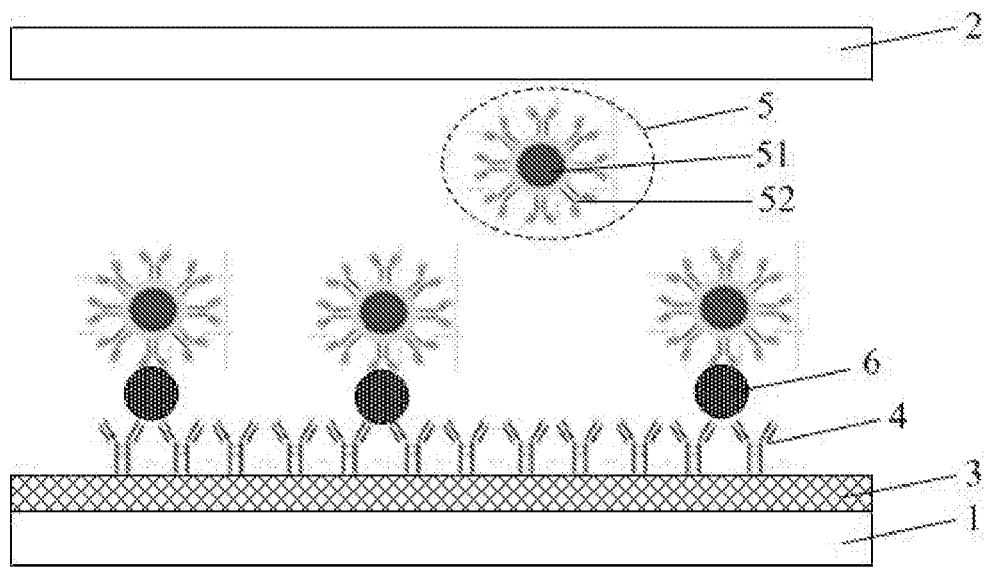
FIG. 14 is a schematic diagram upon adding biological magnetic beads, provided by Embodiment 2 of the disclosure.

Step 2, after a first length of time after adding liquid including antigens to be detected, adding the biological magnetic beads of a first quantity to the detection chamber, as shown in FIG. 14.

Figure 15:
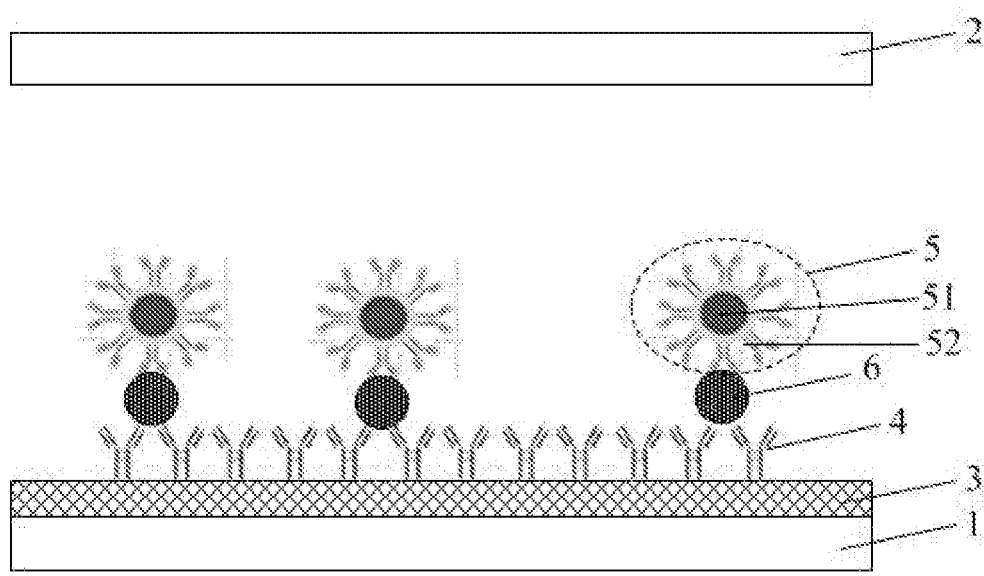
FIG. 15 is a schematic diagram after removing biological magnetic beads which are not bound with antigens, provided by Embodiment 2 of the disclosure.

Step 3, through solution flushing or magnetic field driving, removing the biological magnetic beads which are not bound with the antigens in the detection chamber, as shown in FIG. 15, which is a schematic diagram of a detection chip after biological magnetic beads which are not bound with antigens are removed;

Step 4, applying a first magnetic field to a detection chamber.

Step 5, obtaining a resistivity output by a detection member.

Step 6, according to the corresponding relationship between a prestored resistivity with the number of target antigens, determining the number of the antigens to be detected.

The immunodetection method provided by the embodiment of the disclosure can, by adding biological magnetic beads and antigens to the detection chamber firstly, makes antigens be bound with substrate antibodies of the substrate in the detection chamber and magnetic bead antibodies of biological magnetic beads to form into an integral structure. Then, a magnetic field is applied to the detection chamber. Since magnetic beads of the biological magnetic beads can move under the effect of the magnetic field, the biological magnetic beads bound with antigens can be made to move toward a side wall, where the detection member is disposed, of the detection chamber. When the detection member detects a structural attachment including biological magnetic beads, a change in a corresponding signal is generated, such that according to a signal output by the detection member, information of antigens in a sample to be detected can be determined. Furthermore, a costly optical detection instrument upon immunodetection with an optical signal is not needed, and the problem of strict protection restrictions upon detection with elements including radioactive elements can also be avoided. What is more, the number of antigens in liquid to be detected can be quantitatively detected. As compared with the prior art, by which detection of antigens is influenced by a separation result, since before a reaction of antibodies and antigens it is required to separate antigens from a sample liquid in which antigens originally exist, the disclosure does not need a step for separating antigens, such that no influence of a separation result will be suffered, resulting in high detection accuracy.

Obviously, those skilled in the art can make various modifications and variations to embodiments of the disclosure without departing from the spirit and scope of embodiments of the disclosure. By doing this, if these modifications and variations to the disclosure belong to the scope of the claims of the disclosure and equivalent techniques thereof, the disclosure also intends to include these modifications and variations inside.

The invention claimed is:

1. An immunodetection chip, comprising:
a substrate, and
a cover plate;
   wherein the substrate is disposed opposite to the cover plate to form a detection chamber;
   one side, facing the cover plate, of the substrate is fixedly provided with substrate antibodies, and an inside wall of the detection chamber is provided with a detection member;
   wherein the detection member is located between the substrate and the substrate antibodies, and a biological modification layer is disposed between the substrate antibodies and the detection member;
   wherein the biological modification layer is made of nanogold and directly in contact with the substrate antibodies and the detection member respectively;
   wherein the detection member is configured to output a corresponding electrical signal while adsorbing biological magnetic beads via the biological modification layer;
   wherein the substrate antibodies match with target antigens.

2. An immunodetection device, wherein the immunodetection device comprises the immunodetection chip of claim 1.

3. The immunodetection device of claim 2, wherein the immunodetection device further comprises biological magnetic beads, wherein the biological magnetic beads each comprises a magnetic bead and antibodies enveloping the magnetic bead, and the biological magnetic beads are added to the detection chamber of the immunodetection chip while being used to detect antigens in liquid to be detected.

4. The immunodetection device of claim 2, wherein the immunodetection device further comprises a magnetic field generation member, wherein the magnetic field generation member applies a magnetic field to the immunodetection chip while being used to detect antigens in liquid to be detected.

5. The immunodetection device of claim 4, wherein the magnetic field generation member is located on one side, facing away from the substrate, of the cover plate.

6. The immunodetection device of claim 4, wherein the magnetic field generation member is located on one side, facing away from the cover plate, of the substrate.

* * * * *